US008552145B2

(12) United States Patent
Budzynski et al.

(10) Patent No.: US 8,552,145 B2
(45) Date of Patent: Oct. 8, 2013

(54) VACCINE FOR MODULATING BETWEEN T1 AND T2 IMMUNE RESPONSES

(75) Inventors: Wladyslaw A. Budzynski, Edmonton (CA); R. Rao Koganty, Edmonton (CA); Mark J. Krantz, Edmonton (CA); B. Michael Longenecker, Edmonton (CA)

(73) Assignee: Oncothyreon Inc., Seattle, WA (US)

( * ) Notice: Subject to any disclaimer, the term of this patent is extended or adjusted under 35 U.S.C. 154(b) by 0 days.

(21) Appl. No.: 13/462,314

(22) Filed: May 2, 2012

(65) Prior Publication Data

US 2012/0269884 A1 Oct. 25, 2012

Related U.S. Application Data

(63) Continuation of application No. 10/106,876, filed on Mar. 27, 2002, now Pat. No. 8,198,400.

(60) Provisional application No. 60/278,698, filed on Mar. 27, 2001.

(51) Int. Cl.
*C07K 5/00* (2006.01)
*A61K 39/00* (2006.01)

(52) U.S. Cl.
USPC .................. 530/300; 424/450; 424/184.1

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,837,028 A | 6/1989 | Allen | |
| 4,868,155 A | 9/1989 | Durette et al. | |
| 5,019,369 A | 5/1991 | Presant et al. | |
| 5,019,383 A | 5/1991 | Hopp | |
| 5,580,563 A | 12/1996 | Tam | |
| 5,744,144 A | 4/1998 | Finn et al. | |
| 5,837,249 A | 11/1998 | Heber-Katz et al. | |
| 5,840,839 A | 11/1998 | Wang et al. | |
| 5,871,746 A | 2/1999 | Boutillon et al. | |
| 5,910,306 A | 6/1999 | Alving et al. | |
| 5,993,823 A | 11/1999 | Boutillon et al. | |
| 6,013,779 A | 1/2000 | Wong et al. | |
| 6,015,564 A | 1/2000 | Boutillon et al. | |
| 6,090,406 A | 7/2000 | Popescu et al. | |
| 6,344,203 B1 | 2/2002 | Sandrin et al. | |
| 6,600,012 B1* | 7/2003 | Agrawal et al. ............... | 530/300 |
| 6,683,052 B1* | 1/2004 | Thiam et al. .................. | 424/489 |
| 2002/0018806 A1* | 2/2002 | Agrawal et al. ............... | 424/450 |
| 2002/0051813 A1 | 5/2002 | Boni et al. | |
| 2002/0132771 A1 | 9/2002 | Madiyalakan | |
| 2006/0069238 A1 | 3/2006 | Koganty | |
| 2007/0014844 A1 | 1/2007 | Longenecker | |
| 2008/0131495 A1 | 6/2008 | Longenecker | |

FOREIGN PATENT DOCUMENTS

| | | |
|---|---|---|
| EP | 0093851 | 11/1983 |
| EP | 0203676 | 12/1986 |
| EP | 0230893 | 8/1987 |
| EP | 0491628 | 6/1992 |
| EP | 0945461 | 9/1999 |
| EP | 1065212 | 1/2001 |
| EP | 1182210 | 2/2002 |
| FR | 2776926 A1 | 10/1999 |
| WO | WO-93-21211 | 10/1993 |
| WO | WO-95-27505 | 10/1995 |
| WO | WO-96-40236 A1 | 12/1996 |
| WO | WO-97-34921 A1 | 9/1997 |
| WO | WO-97-38010 A2 | 10/1997 |
| WO | WO98/50527 * | 11/1998 |
| WO | WO-98-510527 | 11/1998 |
| WO | WO-01-12217 A1 | 2/2001 |
| WO | WO-01-18035 A2 | 3/2001 |
| WO | WO-01-36433 | 5/2001 |
| WO | WO-01-70265 | 9/2001 |
| WO | WO 02/43699 | 6/2002 |
| WO | WO-02-076485 | 10/2002 |
| WO | WO-03-089574 A2 | 10/2003 |
| WO | WO-03-094850 | 11/2003 |
| WO | WO-2005-112546 | 12/2005 |

OTHER PUBLICATIONS

"About the Albert B. Sabin Vaccine Institute," Cancer Immunol Immunotherapy 52: S1-S38 (2003).
Alving, "Lipopolysaccharide, lipid A and liposomes containing lipiid A as immunologic adjuvants," Immunobiol 187: 430-446 (1993).
Apostolopoulos et al., "Induction of HLA-A2 restricted CTLs to the mucin-1 human breast cancer antigen," J Immunol 159:5211-5218 (1997).
Bakker-Woudenberg et al., Lipososmes as carriers of antimicrobial agents or immunomodulatory agents in the treatment of infections, Eur. J. Clin. Microbiol. Infect. Dis., 12: 61-67 (1993).
Bartels et al., "Adoptive cellular immunotherapy fo cancer in mice using allogenic T-cells," An Oncology Journal for Surgeons 3: 67-73 (1996).
Benmohamed et al., "High immunogenicity iin chimpanzees of peptides and lipopeptides dervide from four new plasmodium flaciparum pre-erythrocytic molecules," Vaccine 18: 2843-2855 (2000).
Benmohamed et al., "Lipopeptide immunization without adjuvant induces potent and long-lasting B, T helper and cytotoxic T lymphocyte responses against a malaria liver stage antigent in mice and chimpanzees," Eur J Immunol 27: 1242-1253 (1997).
Brossart et al., "Identification of HLA-A2-restricted T-cell epitopes derived from the MUC1 tumor antigen for broadly applicable vaccine therpaies," Blood 93: 4309-4317 (1999).

(Continued)

*Primary Examiner* — Agnieszka Boesen
(74) *Attorney, Agent, or Firm* — Wilson, Sonsini, Goodrich & Rosati

(57) ABSTRACT

The present invention provides liposomal vaccines containing immunogenic lipopeptides that are capable of modulating the humoral and cellular immune responses in vivo.

13 Claims, 1 Drawing Sheet

(56) References Cited

OTHER PUBLICATIONS

Butts et al., "Amulticenter phase IIB randomized study of liposomal MUC1 vaccine for immunotherapy of non-small cell lung cancer (NSCC): L-BLP25 non-small cell cancer study group," Ann Onc 15: 1112 (2004).

Butts et al., "Randomized phase IIB trial of BLP25 liposome vaccine in stage IIIB and IV non-small cell lung cancer," J Clin Onc 23: 6674-6681 (2005).

Carmon et al., "Novel breast-tumor-associated MUC1-derived peptides: characterization in Db-/-X beta 2 microglobulin (beta2m) null mice transgenic for a chimeric HLA-A2. I/Db microglobulin single chain," Int J Cancer 85: 391-397 (2000).

Denton et al., "Sequential order of T and B cell epitope affects immunogenicity but not antibody recognition of the B cell epitope," Peptide Res 7: 258-264 (1994).

Diez-Barra et al., Chemical Abstract, "Solvent free phase transfer catalysis. Improvements on serine O-alkylation," Database accesion No. 127: 220955 (1997).

Engelmann et al., "Identification and topology of variant sequencs within individual repeat domains of the human eptithelial tumor mucin MUC1," J Biol Chem 276: 27764-27769 (2001).

Flinn et al., "Oral absorption studies of lipidic conjugates of thyrotropin releasig hormone (TRH)-1 and luteinizing hormone-releasing hormone (LHRH)," Intl J Pharmaceutics 137: 33-39 (1996).

Fung et al., "Specific immunosuppressive activity of epiglycanin A mucin-like glycoprotein secretedby a murine mammary adenocarcinoma TA3-HA," Cancer Res 51: 1170-1776 (1991).

Gendler et al., "A highly immunogenic region of a human polymorphic epithelial mucin expressed by carcinoma is made up of tandem repeats," J Biol Chem 263: 12820-12823 (1988).

Grohman, et al. Cancer Immunology, 1999, vol. 48, p. 195-203.

Guan et al., "Liposomal formulations of synthetic MUC1 peptides: Effects of encapsulation versus surface display of peptides on immune responses," Bioconjugate Chem. 9: 451-458 (1998).

Gupta et al., "Adjuvants—a balance between toxicity and adjuvanticity," Vaccine 11: 293-306 (1993).

Hanski et al., "Altered glycosylation of the MUC-1 protein core contributes to the colon carcinoma-associated increase of mucin-bound sialyl-lewis expression," Cancer Research 53: 4082-4088 (1993).

Heukamp et al, "Identification of three non-VNTR MUC1-derived HLA-A*0201-restricted T-cell epitopes that induce protective antitumor immunity in HLA-A2/Kb transgenic mice," Int J Cancer 91: 385-392 (2001).

Hiltbold et al., "Naturally processed class II epitope from the tumor antigen MUC1 primes human CD4+ T cells," Cancer Res 58: 5066-5070 (1998).

Karnikas et al., "Antibody and T cell responses of patients with adenocarcinoma immunized with mannan-MUC1 fusion protein," J Clin Invest 100: 2783-2792 (1997).

Karsten et al., Cancer Res 58: 2541-2549 (1998).

Keil et al., "Towards the development of antitumor vaccines: a synthetic conjugate of a tumor-associated MUC1 glycopeptide antigen and a tetanus toxin epitope," Ange chem Int Ed 40: 366-369 (2001).

Kim, "Liposomes as carriers of cancer chemotherapy," Drugs 46: 579-794 (1993).

Kirschenbaumet al, "MUC1 expression in prostate carcinoma: correlation with clinical grade and stage," Molecular Urology 3: 163-167 (1999).

Kudryashov et al., "Toward optimized carbohydrate-based anticaner vaccines: eptiope clustering, carrier structure, and adjuvant all influence antibody responses to Lewis conjugates in mice," PNAS 98: 3264-3269 (2001).

Lopes et al., "Immunoexpression of MUC1 in prostate adenocarcinoma," Virchows Arch 435: 330 (1999).

Lutsiak et al., "Use of a liposome antigen delivery system to alter immune responses in vivo," J Pharmaceutical Sciences 87: 1428-1432 (1998).

MacLean et al., "Prognostic significance of preimmunotherapy serum CA27.29 (MUC-1) mucin level after active specific immunotherapy of metastatic adenocarcinoma patients," J Immunotherapy 20: 70-78 (1997).

Martinon et al., "Immunization of mice with lipopeptides bypasses the prerequisite for adjuvant," J Immunol 149: 3416-3422 (1992).

Meylan et al., "Atom/fragment contribution method for estimating octanol-water partition coefficients," J Pharm Sci 84: 83-92 (1995).

Miller et al., "Vaccination of rhesus monkeys with synthetic peptide ina fusogenicproteoliposome elicits simian immunodeficiency virus-specific CD8+ cytotoxic T lymphocytes," J Exp Med 176: 173-1744 (1992).

Moller et al., "NMR-based determination of the binding epitope and conformational analysis of MUC-1 glycopeptides and peptides bound to the breast cancer-selective monoclonal antibody SM3," Eur J Biochem 269: 1444-1455 (2002).

Mondelli, et al. Journal of Virology, 1994, vol. 68, p. 4829-4836).

Mortara et al.<"Seelctio of virus variants and emergence of virus escape mutatns after immunization with an epitope vaccine," J Virol 72: 1403-1410 (1998).

Mountain, "Revisions in the international system for staging lung cancer," Chest 111: 1710-1717 (1997).

Ng et al., "Prognostic significance of increased immunodetectable MUC-1 in prostate cancer," Proceedings of the American Associaiotn for Cancer Research 38: 542 (1997).

North and Butts, "Vaccination with BLP25 liposome vaccine in stage IIIB and IV non-small cell lung cancer," J Clin Onc 23: 6674-6681 (2005).

Ostro et al., "Use fo liposomes as injectable drug delivery systems," American Journal of Hospital Pharmacy 46: 1576-1587 (1989).

Palmer et al., "Phase I study of the BLP25 (MUC1 peptide) liposomal vaccine for active specific immunotherapy in stage IIIB/IV non-small-cell lung cancer," Clinical Lung Cancer 3: 49-57 (2001).

Papadopoulos et al., "Tumor Angiogenesis is associated with MUC1 overexpression and loss of prostate-specific antigen expression in prostate cancer," Clin Cancer Res 7: 1533-1538 (2001).

Petrakou et al., "Epitope mapping of anti-MUC1 mucin protein core monoclonal antibodies," Tumor Biol 19: 21-29 (1998).

Pihl et al., "Mucinous colorectal carcinoma: Immunopathology and prognosis," Pathology 12: 439-447 (1980).

Price et al., "Summary report on the ISOBM TD-4 workshop: analysis of 56 monoclonal antibodies against the MUC1 mucin," Tumor Biol 19: 1-20 (1998).

Reddish et al., "Pre-immunotherapy serum CA27, 29 (MUC-1) mucin level and CD69+ lymphocytes correlate with effects of theratope sialyl-TN-KLH cancer vaccine in active specific immunotherapy," Cancer Immunology and Immunotherapy 42: 303-309 (1996).

Reichel et al., "Synthetic carbohydrates-based vaccines: synthesis of an L-glycero-D-manno-heptose antigen-T-epitope-lipopeptide conjugate," Chem Comm NEED 2087-2088 (1997).

Sangha et al., "L-BLP25: a peptide vaccine strategy in non-small cell lung cancer," Clin Cancer Res 13: 4652s-4654s (2007).

Sauzet et al., "Long-lasting anti-viral cytotoxic T lymphocytes induced in vivo with chimeric-multiresticted lipopeptides," Vaccine 13: 1339-1345 (1995).

Scher et al., "Post-therapy serum prostate-specific antigen level and survival in patients with androgen-indpendent prostate cancer," J National Cancer Institute 91: 244-251 (1999).

Scherphof et al., "Uptake and intracellular processing of targeted and nontargeted liposomes by rat Kupffer cells in viov and in vitro," Annals New York Academy of Sciences 369-385 (1985).

Scholfield et al., "MUC1 mucin in urological malignancy," BJU Intl 91: 560-566 (2003).

Seth et al., "Evaluation of a lipopeptide immunogen as a therapeutic in HIV type 1-seropositive individuals," Aids Research and Human Retroviruses 16: 337-343 (2000).

Springer et al., "T and Tn, general carcinoma autoantigens," Science 224: 1198-1206 (1984).

Toyokuni et al., "Synthetic vaccines: synthesis of a dimeric Tn antigen-lipopeptide conjugate that elicits immune responses against Tn-expressing glycoproteins," J Am Chem Soc 116: 395-396 (1994).

Tsunoda et al., "Lipopeptide particles as the immunologically active component of CTL inducing vaccines," Vaccine 17: 675-685 (1999).

Vitiello et al., "Development of a lipopeptide-based therapeutic vaccine to treat chronic HBV infection," The Journal of Clinical Investigation Jan. 1995 pp. 341-349.

Von Mensdroff-Pouilly et al., "Reactivity of natural and induced human antibodies to MUC1 mucin with MUC1 peptides and N-acetylgalctosamine (GalNac) peptides," Int J Cancer 86: 702-712 (2000).

Von Mensdroff-Pouilly et al., "Survival in early breast cancer patients 1 sfavorably influenced by a natural humoral immune response to polymorphic epithelial mucin," J Clin Oncol 18: 574-583 (2000).

Von Mensdroff-Pouilly et al., Abstract Only, "Human MUC1 mucin: a multifaceted glyocprotein," Int J Biol Markers 15: 343-356 (2000).

Wassef et al., "Liposomes as carriers for vaccines," Immunomethods 4: 217-222 (1994).

Wilkinson, et al. Bioconjugate Chemistry, 1998, vol. 9, p. 539-547.

Zeng et al., J Peptide Science 2: 86-92 (1996).

Agrawal et al., "In vitro induction of MUC-1 peptide-specific type 1 T lymphocyte and cytotoxic T lymphocyte responses from healthy multiparous donors," Journal of Immunology 157: 2089-95 (1996).

Gagliardi et al., "Presentation of peptides by cultured monocytes or activated T cells allows specific priming of human cytotoxic T lymphocytes in vitro," International Immunology 7: 1741-1752 (1995).

Morse, M.A. Technology Evaluation: BLP-25, Biomira Inc. Curr. Opin. Mol. Ther. Feb. 2001, vol. 3, No. 1, pp. 102-105.

Parra et al., "Characterization of conserved T- and B-Cell epitopes in plasmodium falciparum major merozoite surface protein 1," Infection and Immunity 68: 2685-2691 (2000).

Pantuck, et al. "Phase I trial of Antigen-Specific Gene Therapy Using a Recombinant Vaccinia Virus Encoding MUC-1 and IL-2 in MUC-1—positive patients with adavanced cancer." J Immunother. May-Jun. 2004, vol. 27, No. 3, 240-253.

Schut, et al. "MUC1 Expression, Splice Variant and Short Form Transcription (MUC1/Z, MUC1/Y) in Prostate Cell Lines and Tissues." BJU International Feb. 2003, vol. 91, No. 3, 278-283.

Vordermeier et al., "Promiscuous T cell recognition of an H-2 IA-presented mycobacterial epitope," Euro J Immunol 24; 2061-2067 (1994).

\* cited by examiner

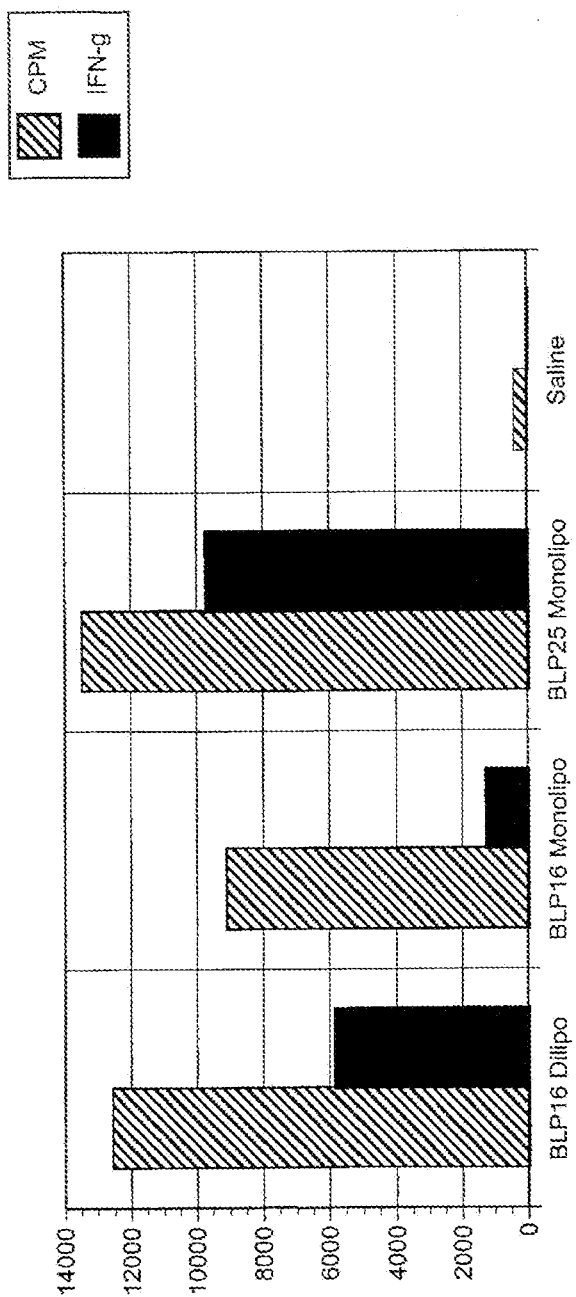

VACCINE FOR MODULATING BETWEEN T1 AND T2 IMMUNE RESPONSES

CROSS-REFERENCE TO RELATED APPLICATIONS

The present application is a continuation of U.S. application Ser. No. 10/106,876, filed Mar. 27, 2002 now U.S. Pat. No. 8,198,400, which claims priority to U.S. provisional application No. 60/278,698 filed on Mar. 27, 2001, all of which are herein incorporated by reference in their entireties.

SEQUENCE LISTING

The instant application contains a Sequence Listing which has been submitted via EFS-Web and is hereby incorporated by reference in its entirety. Said ASCII copy, created on Apr. 30, 2012, is named 34395-812-301-Sequence-Listing.txt and is 8 Kilobytes in size.

FIELD OF THE INVENTION

The present invention provides liposomal vaccines capable of modulating the immune response in vivo, particularly the humoral and cellular immune responses.

BACKGROUND OF THE INVENTION

To effectively combat disease, a vaccine should ideally stimulate several immunological reactions, such as the production of antibodies (humoral immunity) and the mobilization of immunological cells (cellular immunity).

A cellular immune response brings about a proliferation and stimulation of T-lymphocytes, such as cytotoxic (CTL) and delayed-type hypersensitivity (DTH) T-cells, which go on to activate macrophages and impede the propagation of pathogens. The induction of a humoral response causes the body's B-cells to produce antibodies against the offending pathogen. However, some intracellular pathogens and retroviruses survive and are extremely resistant to humoral-based immune responses and require the stimulation of cytotoxic T-cells to destroy such biological invaders.

Synthetic peptides are often used as antigenic epitopes and can be tailor-made using standard peptide synthesis technologies so that they induce minimal side effects. However, such peptides typically invoke a relatively weak immunogenic response.

Nonetheless, immunogenicity can be boosted by attaching a lipid to the synthetic peptide. It has been shown, for example, that lipidation of synthetic peptide antigens leads to the induction of strong T-cell proliferation, CTL, and antibody responses in immunized mice, chimpanzees, or humans (BenMohamed et al., *Vaccine*, 18, 2843-2855 (2000); Gahery-Segard et al., *J. Virology.*, 74, 1694-1703 (2000); Seth et al., *AIDS Res. Hum. Retroviruses*, 16, 337-343 (2000); Tsunoda et al., *Vaccine*, 17, 675-685 (1999); BenMohamed et al., *Eur. J. Immunol*, 27, 1242-1253 (1997); Vitiello et al., *J. Clin. Invest.*, 95, 341-349 (1995)).

A preparation of such antigens may be delivered in vivo using a vaccine "carrier," but the carrier itself can become the target of the host's humoral immune response. Thus, the host's antibodies act against the vaccine carrier and not the antigenic epitope, which can result in rapid clearance of the vaccine by anti-carrier antibodies, negating the usefulness of the actual vaccine.

The incorporation of the lipid moiety of a lipopeptide into a liposome, however, proves an extremely useful way in which to deliver an antigen in vivo without eliciting an immune response against the carrier. However, none of these advances assist in the modulation of one immune response to another. That is, it has not previously been shown that a liposomally-bound lipopeptide can elicit cellular and humoral immune responses by altering the number of lipids attached to a single peptide.

The present invention, however, provides a novel way of invoking and modulating between cellular and humoral immune responses by using a single antigenic peptide and a carrier that does not stimulate humoral responses against itself.

SUMMARY OF THE INVENTION

The invention is directed to a formulation of liposomes containing immunogenic lipopeptides. The present invention is further directed to the administration of such liposomes in formulations that are capable of both invoking and modulating an immune response in an individual.

In one embodiment, the invention provides a method for producing immunogenic liposomes comprised of self assembling lipids, including lipid-derivatives of immunogenic peptides. The liposomal formulation can contain and deliver either monolipopeptides, dilipopeptides, or mixtures of each to invoke and, thereby, modulate a cellular, humoral, or cellular and humoral immune responses, respectively. The peptide is an immunogenic sequence of amino acids, representing an epitope or a similar feature that is antigenic in nature.

Another embodiment of the invention provides a composition that can stimulate and modulate an immune response. Such a composition comprises a liposomal vesicle, wherein the lipid bilayer of the liposomal vesicle comprises at least one immunogenic monolipopeptide and at least one dilipopeptide, wherein the percentage of the monolipopeptide varies from more than about 0 to less than about 100% and wherein the percentage of the dilipopeptide varies from more than about 0 to less than about 100%.

Yet another embodiment of the invention provides a method of stimulating a cellular immune response comprises administering to a patient an effective amount of at least one monolipopeptide and at least one dilipopeptide, wherein the monolipopeptide and the dilipopeptide are associated with the same or different liposomal vesicle. In one embodiment, the percentage of the monolipopeptide administered is more than about 50%. The percentage of the monolipopeptide can also be more than about 70% or more than about 90%.

Yet another aspect of the invention provides a method of stimulating a humoral immune response comprising administering to a patient an effective amount of at least one monolipopeptide and at least one dilipopeptide, wherein the monolipopeptide and the dilipopeptide are associated with the same or different liposomal vesicle. In one embodiment, the percentage of the monolipopeptide administered is more than about 50%. The percentage of the monolipopeptide can also be more than about 70% or more than about 90%.

The present invention also encompasses compositions wherein the peptide portion of the monolipopeptide or the dilipopeptide is derived from a protein associated with a disease selected from the group consisting of tuberculosis, hepatitis B, malaria, and cancer. In a preferred embodiment, the peptide comprises at least 5 contiguous amino acids of an immunogenic region of the protein. In a more preferred embodiment, the monolipopeptide or the dilipopeptide is designed from a MUC-1 protein sequence. In an even more preferred embodiment, the MUC-1 lipopeptide comprises the sequence GVTSAPDTRPAPGSTA (residues 2 to 16 of SEQ ID NO: 1). In another preferred embodiment, the monolipopeptide or the dilipopeptide is designed from a tuberculosis lipopeptide comprising the sequence DQVHFQPLPPAVVKLSDALIK (SEQ ID NO: 2). In another preferred embodiment, an antigenic MUC-1 peptide of the present invention can be selected from any part of the sequence SGVTSAPDTRPAPGSTAPPAHGVTSAPDTRPAPGSTAPPAHGVSSL (SEQ ID NO. 1).

In another embodiment, the monolipopeptide or the dilipopeptide is designed from a tuberculosis peptide. In a more preferred embodiment, the tuberculosis peptide has the sequence, DQVHFQPLPPAVVKLSDALIK (SEQ ID NO. 2).

In yet another embodiment, the instant invention uses a lipidated antigenic hepatitis B peptide. In a preferred embodiment, the hepatitis B peptide has the sequence, IRTPPAYRPPNAPILK (SEQ ID NO. 3). In another preferred embodiment, a malaria peptide may be modified to contain lipids. In one preferred embodiment, the malaria peptide has the sequence, VTHESYQELVKKLEALEDAVK (SEQ ID NO. 4).

A method of stimulating both a cellular and humoral immune response comprising administering to a patient an effective amount of at least one monolipopeptide and at least one dilipopeptide is also provided. Another aspect of the present invention provides a method of modulating between a cellular and humoral immune response, comprising simultaneously administering a formulation comprising a liposomally-bound monolipopeptide and a formulation comprising a liposomally-bound dilipopeptide. Yet another aspect of the present invention provides a method of modulating between a cellular and humoral immune response, comprising first administering a formulation comprising a liposomally-bound monolipopeptide and then administering a formulation comprising a liposomally-bound dilipopeptide. Yet another aspect provides a method of modulating between a cellular and humoral immune response, comprising first administering a formulation comprising a liposomally-bound dilipopeptide and then administering a formulation comprising a liposomally-bound monolipopeptide. A method of stimulating a cellular and humoral immune response, comprising administering an effective amount of a formulation comprising a liposomally-bound dilipopeptide is also provided.

Both the foregoing general description and the following brief description of the drawing and the detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE DRAWINGS

FIG. 1 shows T cell proliferation and IFN-g levels in C57BL/6 mice immunized two times with MUC1 Dilipo- or Monolipopeptides in liposomes (Protocol I346). FIG. 1 shows C57BL/6 mice were immunized subcutaneously two times with a standard BLP25 liposomal vaccine, or with 16aa MUC1 based Dilipo- or Monolipopeptide liposomal vaccines. Nine days after a second immunization procedure a T cell proliferation and IFN-g levels were tested in standard assays.

DETAILED DESCRIPTION OF THE INVENTION

An unexpected and surprising finding of the present invention is that the induction of immune responses in vivo can be modulated by administering serially, or in combination, liposomally-bound peptides comprising one lipid chain and liposomally-bound peptides comprising at least two lipid chains.

The term "modulate" means some change, adjustment, or adaptation to a certain proportion. Thus, an immune response may be modulated by stimulating factors which bring into play a change in immunological activity. The intensity of an immune response may also be modulated. For example, the intensity or level of T-cell proliferation can be made greater or lower after administration of factors that effect modulation. In the present invention, those factors can be liposomally-bound lipopeptides.

It was surprisingly discovered that a peptide having one lipid chain may invoke a large cellular immune response (i.e., a "T1" immune response) when incorporated into a liposomal formulation, but only a minimal or no humoral response. However, that same peptide, when incorporated into a liposome, can be made to induce a large humoral response (i.e., a "T2" response), accompanied by either a minimal or massive cellular response, when two lipids are attached to its surface. The range of cellular response observed with a lipopeptide varies depending upon the identity of the lipopeptide. The presence of one, two, or more than two lipids on an antigenic peptide may also increase or reduce the intensity by which an immune response is activated. The intensity of an immune response and the type of immune response that is stimulated can also be modulated by varying the number of amino acid residues between two lipids on an antigenic peptide.

The present invention demonstrates that attaching more than one lipid chain to a peptide bound to a liposomal bilayer stimulates a largely humoral immune response, along with variable cellular activity ranging from minimal to massive. The present invention also shows that attaching a second lipid to an antigenic peptide increases the level of T-cell proliferation as well as inducing antibody production as compared to the monolipid derivative. The term "derivative" means a compound derived or obtained from another that contains essential elements of the parent substance. Thus, the lipid derivative of an antigen refers to a peptide that has at least one lipid attached. Hence it is possible to administer an effective amount of a liposomal formulation comprising only dilipopeptides to invoke antibody production and cellular activity. An "effective amount" of liposomally-bound lipopeptide formulation, refers to an empirically-derived amount of that lipopeptide that modulates an immune response.

It was also discovered that for some antigens a dilipopeptide lipsomal formulation will trigger a massive cellular response, in addition to a large humoral response.

Specifically, the examples show that liposomal formulations having a monolipopeptide induced largely cellular responses and minimal humoral responses, and liposomal formulations having a dilipopeptide induced largely humoral responses and minimal cellular responses, for MUC-1, tuberculosis, and hepatitis B peptides. Administering a combination of a di- and a monolipopeptide resulted in superior cellular and humoral responses.

Another advantage of the present invention is that different lipopeptides can be incorporated into a liposome and thus be transported and presented to the immune system simultaneously and under the same conditions. Thus, it is possible to induce in an individual multiple immune responses by treating that individual with a liposome that contains a T1-inducing monolipopeptide and a T2-inducing dilipopeptide. Alternatively, a mixture of liposomally-bound monolipopeptides and liposomal-bound dilipopeptides can also be used to simultaneously induce multiple immune responses.

Thus, the present invention provides novel compositions and methods for modulating an immune response by varying the number of lipids that are attached to an antigenic peptide. An immune response can be modulated by adding a two or more lipids to an antigenic peptide, as can the intensity of the immune response. Furthermore, the intensity of an immune response can be modulated by varying the spacing of amino acids between lipids.

An immune response can also be invoked by injecting pre-stimulated antigen-presenting cells or T-cells into a patient. Known as "adoptive immunotherapy," this technique creates in vitro an expanded population of antigen-specific cells that are primed to combat the causative agent once reintroduced into the body. In essence, cells are removed from the patient, stimulated in vitro and reinjected back into the patient's bloodstream. Specifically, peripheral blood lymphocytes, such as antigen presenting cells, are isolated and then "charged" by exposing the cells to antigens in vitro. The antigen becomes endocytosed by an antigen presenting cell, whereupon it becomes associated with a major histocompatibility complex and subsequently presented on the outer surface of the cell. This population of primed cells can then be reinjected into the patient. Fractionating the peripheral blood lymphocytes into dendritic cells and/or macrophages prior to charging can also be performed.

Thus, a liposomal formulation of the present invention, comprising membrane-bound, antigenic lipopeptides can be added to the isolated antigen presenting cells in vitro to "charge" them. For example, a liposomal formulation comprising a monolipo-MUC I peptide, a dilipo-MUC I peptide, or a combination of both peptides, can be used to charge peripheral blood lymphocytes which are then reinjected into the patient as a cellular vaccine.

Alternatively, "adoptive T-cell transfer therapy" can be performed. This entails incubating a patient's T-cells with pre-charged antigen presenting cells in vitro. The T-cells become activated and are re-administered to a patient suffering from, for example, an adenocarcinoma. For a description of art-recognized techniques for adoptive T-cell transfer therapy, see Bartels et al, *Annals of Surgical Oncology*, 3(1): 67 (1996), incorporated by reference. Thus, according to the present invention, a lipidated antigenic peptide is selected, incorporated into a liposome, and used to stimulate peripheral blood lymphocytes, which can either be injected back into the patient or used themselves to activate isolated T-cells. A T-cell activation method is also useful for generating cytotoxic and helper T-cell responses to antigens involved in various pathological conditions, such as cancer, tumors, viral infections, and bacterial infections.

Lipsomes

Liposomes are microscopic vesicles that consist of one or more lipid bilayers surrounding aqueous compartments. See e.g., Bakker-Woudenberg et at, *Eur. J. Clin. Microbiol. Infect. Dis.* 12 (Suppl. 1): S61 (1993) and Kim, *Drugs,* 46: 618 (1993). Because liposomes can be formulated with bulk lipid molecules that are also found in natural cellular membranes, liposomes generally can be administered safely and are biodegradable.

Depending on the method of preparation, liposomes may be unilamellar or multilamellar, and can vary in size with diameters ranging from about 0.02 μm to greater than about 10 μm. A variety of agents can be encapsulated in liposomes. Hydrophobic agents partition in the bilayers and hydrophilic agents partition within the inner aqueous space(s). See e.g., Machy et al., LIPOSOMES IN CELL BIOLOGY AND PHARMACOLOGY (John Libbey, 1987), and Ostro et al., *American J. Hosp. Pharm.* 46: 1576 (1989).

Liposomes can adsorb to virtually any type of cell and then release an incorporated agent. Alternatively, the liposome can fuse with the target cell, whereby the contents of the liposome empty into the target cell. Alternatively, a liposome may be endocytosed by cells that are phagocytic. Endocytosis is followed by intralysosomal degradation of liposomal lipids and release of the encapsulated agents. Scherphof et al., *Ann. N.Y. Acad. Sci,* 446: 368 (1985).

Other suitable liposomes that are used in the methods of the invention include multilamellar vesicles (MLV), oligolamellar vesicles (OLV), unilamellar vesicles (UV), small unilamellar vesicles (SUV), medium-sized unilamellar vesicles (MVV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). The skilled artisan will recognize that the techniques for preparing these liposomes are well known in the art. See COLLOIDAL DRUG DELIVERY SYSTEMS, vol. 66 (J. Kreuter, ed., Marcel Dekker, Inc., 1994).

Lipids

A "lipid" may be a myristyl, palmitoyl, or a lauryl molecule, that can be attached to amino acids that possess functional oxygen, nitrogen, or sulfur groups. Such amino acids include, but are not limited to, threonine, serine, lysine, arginine, and cysteine amino acids. A "monolipopeptide" is a peptide to which only one lipid chain is attached. Similarly, a "dilipopeptide" is a peptide that has two lipid chains attached to one or two amino acids. If the two lipid chains are attached to two amino acid residues, those residues can be spaced any number of amino acids apart.

A "liposomal formulation" describes in vitro-created lipid vesicles in which mono- and/or dilipopeptides can be incorporated. Thus, "liposomally-bound" refers to a peptide that is partially incorporated or attached to a liposome. A liposomal formulation may also be referred to
as a "liposomal vaccine." A liposomal formulation may comprise two types of liposomes; one that contains mostly, if not all, monolipopeptides incorporated into its structure, and a second that contains mostly, if not all, dilipopeptides in its structure. Individual preparations of "mono-" and "di-" liposomes can be administered together to modulate an immune response, even though the monolipopeptide and dilipopeptide do not exist on one liposome.

When incorporated into a liposome, the monolipopeptide and the dilipopeptide may be peptides that are the same antigenic epitope. Alternatively, the peptide sequences for each lipopeptide may comprise different epitopes. The lipopeptides may be antigens that are associated with the same or different proteins.

A lipopeptide can be incorporated into liposomes because the lipid portion of the peptidic molecule will spontaneously integrate into the lipid bilayer. Thus, a lipopeptide may be presented on the "surface" of a liposome. Alternatively, a peptide may be encapsulated within a liposome. Techniques for preparing liposomes and formulating them with molecules such as peptides are well known to the skilled artisan.

Exemplary Adjuvants

The present liposomal vaccines may also be formulated advantageously with an adjuvant. As conventionally known in the art, adjuvants are substances that act in conjunction with specific antigenic stimuli to enhance the specific response to the antigen. Monophosphoryl lipid A (MPLA), for example, is an effective adjuvant that causes increased presentation of liposomal antigen to specific T Lymphocytes. Alving, C. R., *Immunobiol,* 187:430-446 (1993). The skilled artisan will recognize that lipid-based adjuvants, such as Lipid A and derivatives thereof, are also suitable. A muramyl dipeptide (MDP), when incorporated into liposomes, has also been shown to increase adjuvancity (Gupta R K et al., Adjuvants-A balance between toxicity and adjuvancity, "*Vaccine,* 11, 293-306 (1993)).

Another class of adjuvants includes stimulatory cytokines, such as IL-2. Thus, the present liposomal vaccines may be formulated with IL-2, or IL-2 may be administered separately for optimal antigenic response. IL-2 is beneficially formulated with liposomes.

Exemplary Vaccine Formulations

Vaccines may also be formulated with a pharmaceutically acceptable excipient. Such excipients are well known in the art, but typically should be physiologically tolerable and inert or enhancing with respect to the vaccine properties of the inventive compositions. Examples include liquid vehicles such as sterile, physiological saline. An excipient may be added at any point in formulating a liposomal vaccine or it may be admixed with the completed vaccine composition.

Vaccines may be formulated for multiple routes of administration. Specifically preferred routes include intramuscular, subcutaneous, or intradermal injection, aerosol, or oral administration, or by a combination of these routes, administered at one time or in a plurality of unit dosages. Administration of vaccines is well known and ultimately will depend upon the particular formulation and the judgement of the attending physician. Vaccine formulations can be maintained as a suspension or they may be lyophilized and hydrated later to generate a useable vaccine.

To provide greater specificity, thus reducing the risk of toxic or other unwanted effects during in vivo administration, it is advantageous to target the inventive compositions to the cells through which they are designed to act, namely antigen-presenting cells. This may conveniently be accomplished using conventional targeting technology to direct a liposome containing an immunogenic peptide to a particular location within the body. To target antigen presenting cells, for example, mannose and the Fc portion of antibodies can be chemically conjugated to an antigenic peptide, or by recombinantly fusing the targeting peptide to the immunogenic lipopeptide. Other, similar strategies will be familiar to the practitioner.

Exemplary Quantities of Lipopeptides and Liposomal Formulations

The ratio of antigenic monolipopeptides and dilipopeptides within a liposome can be varied so as to modulate an immune response to different degrees of intensity. For example, increasing the amount of dilipopeptide incorporated in a liposome relative to the amount of monolipopeptide may make the resulting formulation more humoral-inducing. Of course, due to differing magnitudes of response to different antigens, different ratios may be needed to achieve the desired balance of humoral and cellular response.

For example, the skilled artisan can create liposomes made up of a ratio of covalently linked, immunogenic monolipopeptides and dilipopeptides, wherein the percentage of the monolipopeptide varies from more than about 0 to less than about 100% of the liposome. Similarly, the dilipopeptide can be present in the liposomal membrane as a percentage of more than about 0 to less than about 100%. For example, a liposome comprising 75% monolipopeptide and 25% dilipopeptide may generate a largely T1 immune response with some T2 activity. The present invention provides methods for creating a liposome comprising about 1 to about 30% monolipopeptide, about 30 to about 50% monolipopeptide, or about 50 to about 99% monolipopeptide. Similarly, a liposome comprising about 1 to about 30% dilipopeptide, about 30 to about 50% dilipopeptide, or about 50 to about 99% dilipopeptide can also be created. Thus, the present invention enables the creation of liposomes containing, for example, monolipopeptide: dilipopeptide in ratios such as about 10%:about 90%, about 30%:about 70%, about 50%:about 50%, about 70%:about 30%, about 90%:about 10% and about 99%:about 1%. Determining relative antigenicity is within the purview of one having ordinary skill in immunology.

An effective amount of a liposomal formulation containing at least one monolipopeptide and at least one dilipopeptide can be administered to a patient, wherein the monolipopeptide and dilipopeptide are associated with either the same or different liposomal vesicle. Thus a single liposomal formulation comprising a ratio or ratios of a monolipopeptide and a dilipopeptide can be administered to a patient to invoke a desired immune response; or alternatively, combinations of at least two liposomal formulation comprising different ratios of a monolipopeptide and a dilipopeptide can be administered to a patient to invoke a similar or different immune response.

"Treating" in its various grammatical forms in relation to the present invention refers to preventing, curing, reversing, attenuating, alleviating, minimizing, suppressing, or halting the deleterious effects of a disease state, disease progression, disease causative agent, or other abnormal condition.

Exemplary Immunogenic Peptides Useful in the Invention

Any peptidic antigen or epitope may be lipidated and incorporated into a liposome for the purposes of inducing or modulating immune responses in vivo. One, two, or more than two lipids can be added to any part of a peptide. The skilled artisan will recognize that the antigenic peptide is selected based upon the type of disease affecting the individual. For example, a "MUC-1" antigen is useful for making antigen-specific T-cells that can be used in treating adenocarcinoma. Similarly, a tuberculosis peptide, hepatitis B peptide, or a malaria peptide all can be lipidated according to the present invention and used to invoke cellular and humoral immunity as desired to treat the specific diseases with which the peptides are associated. The present invention is not limited to the use of MUC-1, tuberculosis peptides, hepatitis B peptides, or malaria peptides as liposomally-bound lipopeptidic vaccines.

A variety of immunogenic peptides can be lipidated and incorporated into liposomal membranes to create a number of different immunogenic-specific vaccines. Described herein, for example, is the immunogenic effect of lipidation upon a mucin-derived peptide. MUC I mucins are macromolecular glycoproteins expressed in all epithelial cells of healthy individuals. The core peptidic sequence of MUC-1 comprises 20 amino acid residues that are repeated throughout the protein anywhere from 60 to 120 times. The repeated sequence, GVT-SAPDTRPAPGSTAPPAH (SEQ ID NO: 19), has five potential sites for glycosylation (bolded S, serine and T, threonine) and an immunogenic "DTR" epitope (underlined).

Generally, carbohydrates are linked to one or more of the serine or threonine residues as O-linked structures and when all five sites are glycosylated, the epitope is concealed. In cancer cells, however, the glycosylation step is prematurely terminated such that the resultant carbohydrates are truncated. Consequently, the DTR epitope is exposed and the peptidic core sequence and the carbohydrates become immunogenic. Thus, this peptide sequence is one example of an epitope that may be used in the context of the present invention so as to induce and modulate an immune response. For example, an antigenic MUC I peptide of the present invention can be selected from any part of the sequence SGVTSAP-DTRPAPGSTAPPAHGVTSAPDTRPAPG-STAPPAHGVSSL (SEQ ID NO. 1) and lipidated so as to contain one, two, or more than two lipids.

The size of an immunogenic peptide is also subject to variation. Lipidated MUC-1 peptidic molecules ranging from 16 (1882 Daltons) to 40 (5050 Daltons) amino acids in size, for example, invoke immune responses as described in the present invention. However, such immunogenic peptides are not limited by size and may be a portion or even all of the desired immunogen. Typically, small peptide antigens are preferred, due to ease of manufacture and greater specificity. Thus, SGVTSAPDTRPAPGSTA (residues 1 to 17 of SEQ ID NO: 1) and STAPPAHGVTSAPDTRPAPGSTAPP (residues 15 to 39 of SEQ ID NO.: 1) are smaller MUC-1 peptides that can be lipidated according to the present invention. Accordingly, unless they are multimeric multiple copies of the same epitope), most antigens will comprise from about 9 to about 100 amino acids. More specifically, antigens that are about 9 to about 20, about 20 to about 40, about 40 to about 60, about 60 to about 80, and about 80 to about 100 amino acids in size can be lipidated and incorporated into liposomes as described. Fragments of protein antigens can be produced by recombinant DNA techniques and assayed to identify particular epitopes. Preferably, small peptides are produced by in vitro synthetic methods and assayed. Thus, any antigenic sequence in whole, or in part, may be used in a lipidated form according to the instant invention. By "whole, or in part" it is meant that either the entire antigenic peptide or some smaller peptide derived from the larger may be lipidated. A "smaller peptide" may be a fragment of a larger peptide antigen or may be synthesized recombinantly or chemically.

Other illustrative examples of peptides that can be synthesized, lipidated, and used in liposomally prepared vaccines include, but are not limited to, peptides involved in tuberculosis, hepatitis B, malaria, and cancer diseases.

The tuberculosis peptide DQVHFQPLPPAVVKLSDA-LIK (SEQ ID NO. 2), which originates from a 38 kDa secretory protein of Mycobacterium tuberculosis, can be made with One or two lipids and formulated into liposomal formulations described above.

Similarly, a hepatitis B antigenic peptide is represented by the amino acid sequence IRTPPAYRPPNAPILK (SEQ ID NO. 3). Likewise, the malaria peptide VTHE-SYQELVKKLEALEDAVK (SEQ ID NO. 4) also can be formulated into a liposomal vaccine.

An amino acid, such as threonine, serine, lysine, arginine, or cysteine, which occurs within the natural sequence of an antigenic peptide, may be a convenient site to which a lipid can be linked. Alternatively, any one of these amino acids can be added to either end or within a peptide sequence so as to facilitate the linking of a lipid moiety. Thus, an antigenic peptide can be made to have two lysine residues at its carboxyl terminus so as to facilitate the linking of two lipids. By "made" the present invention contemplates the use of conventional peptide synthesis methods to introduce one or more additional amino acids to a peptide sequence. However, recombinant methods also can be employed to design polynucleotides that encode the desired amino acid sequence. Thus, the present invention envisions the chemical and recombinant synthesis of antigenic peptides that are amenable to lipidation.

Throughout the specification, any and all references to a publicly available document, including a U.S. patent, are specifically incorporated by reference.

The examples below are intended to illustrate but not limit the invention. While they are typical of those that might be used, other procedures known to those skilled in the art may be used.

Example 1

The purpose of this example was to determine the T-cell proliferation response and the Anti-MUC-1 antibody levels in response to administration of a MUC-1 antigen liposomal vaccine.

Summary of Procedures Used (i) Immunization

MUC1 based liposomal vaccines ("BLP25 liposomal vaccines") at a dose of 100 µg (250 µl) was injected subcutaneously, two, three, or four times, at biweekly intervals, into right and left inguinal regions (125 µl per each site).

(ii) T-Cell Proliferation Assay

Nine days after the last immunization with BLP25 liposomal vaccine all mice were sacrificed and lymph nodes were surgically excised. Nylon wool purified lymph node T-cells were then cultured with antigen presenting cells (APCs), which were obtained from the spleens of naïve mice of the same strain and treated with mitomycin C. These mixed cultures were pulsed with MUC1 derived synthetic lipopeptide (BP1-148) and control peptide (BP1-72) for four days. After the fourth day, some supernatants were collected for IFN-g assay, and the cultures were then pulsed with a fresh medium that contained a tritium labelled thymidine. After a further 18-20 hours the incorporation of DNA-incorporated tritium was counted in a liquid scintillation counter.

(iii) IFN-Gamma Assay

IFN-γ levels in collected supernatants were determined by a specific ELISA using a sandwich technique. Briefly, 96 well Maxisorp flat bottom plates (Nunc, Denmark) were coated with 50 ul of catcher monoclonal antibody R4.6A2 (Biomira, lot# IM98A20A) for 35 min at 37° C., 5% $CO_2$. The plates were then washed and incubated 45 minutes with test samples and with positive standard cytokine sample (Pharmingen lot# M031554).

After two washes the second biotinylated antibody was added: XMG1.2 (Biomira lot# BG98G02B). After washing, peroxidase-conjugated streptavidin (Jackson ImmunoResearch lot#42350) was added and again incubation was 30 minutes. After 5 washes, 100 µl of HRPO substrate solution: 1 µl of 30% $H_2O_2$ diluted in 10 mL of 1 mg/mL ABTS (Aldrich lot#01328ES) buffered with citric acid and $Na_2HPO_4 \cdot 7H_2O$ was prepared immediately before use and added to each well. The optimal density was measured with Thermomax ELISA reader at 405 nm wavelength in kinetic mode for 10 minutes. Cytokine levels in the test sample were determined by comparison with reference standards.

(iv) Anti-MUC1 Antibody Levels

Microtiter 96 well plates were coated with BP1-151HSA conjugate (MUC1 24 amino acid peptide conjugated to HSA), or with Blend C (Blend C is a natural human MUC1 mucin purified from ovarian cancer ascites). Serial dilutions of sera were incubated on the antigen coated plates at room temperature for 1 hr, after which the wells were thoroughly washed. Peroxidase-labeled goat anti-mouse IgG specific antibody was added and incubated at room temperature for 1 hr. Each plate was then washed and ABTS substrate was added. After 15 min the absorbance at 405 nm was measured on an ELISA reader.

Example 2

Mono- and Dilipidated MUC I Antigenic Peptides

The purpose of this example was to demonstrate that a liposomally-bound MUC I peptide with two lipid chains dramatically increases the production of anti-MUC I antibodies in immunized mice as compared to a MUC I peptide with one lipid.

MUC 1 peptides were chemically synthesized to contain one or two lipids. "BP1-217" (SEQ ID NO: 5) has two liposerine residues attached at the carboxy terminus of the core peptidic sequence and "BP1-228" (SEQ ID NO: 6) has only one liposerine attached to the carboxy terminus. The monolipopeptide and dilipopeptide were separately incorporated into liposomes and the resultant liposomal formulations were evaluated as vaccines.

```
BP1-217:
GVTSAPDTRPAPGSTAS(myristyl)S(myristyl)L

BP1-228:
GVTSAPDTRPAPGSTAS(myristyl)L
```

After at least two subcutaneous immunizations of C57BL/6 mice with the dilipopeptide liposomal vaccine, BP1-217, induced the T2, humoral response, producing very high levels of anti-MUC I immunoglobulin G (IgG). In contrast, a cellular response with very low levels of IgG produced was invoked in mice immunized two times with the monolipopeptide, BP1-228. For example, BP1-217 produced anti-MUC I IgG titers in the range of 1/72,000 to 1/218,700 on BP1-151 HSA solid phase and 1/100-1/2700 titers on Blend C solid phase, whereas BP1-228 produced only low titers of IgG antibodies on BP1-151 HSA solid phase, and no antibodies were detected on Blend C solid phase. See Table 1, below.

BP1-228 or BLP-25, as monolipopeptides, produced very low or no antibody levels as compared to any MUC1 peptide with 2 lipid chains. All formulations tested are liposomal and contain lipid A adjuvant.

Anywhere from 40-100 μg of MUC1 lipopeptide can be used per immunization, although the present invention is not limited to these amounts, which may also vary according to the specific peptide used. 5 μg of MUC1 peptide into liposomes elicited a strong T1 immune response, but no antibody production. In clinical trials, a 1000 μg dose of BLP25 injected into patients was found to be very effective in eliciting a specific T cell proliferation.

It is also shown that quantitative rather than qualitative differences between lipid chains are important in eliciting T1 or T2 responses. That is, a humoral immune response can be elicited regardless of the type of lipid chain attached to the peptide. For instance, a MUC-1 peptide, "BP1-132A" (SEQ ID NO:7), that has two palmitoyl lysine lipophilic amino acid residues attached to two adjacent lysine residues was also shown to induce humoral immunity. See Table 2.

BP1-132A:

TAPPAHGVTSAPDTRPAPGSTAPPK(palmitate)K(palmitate)G

TABLE 1

Protocol 1346 IoG Antibody Titer Data Summary

| Infected Material | Mouse # | BP1-151-HSA Log₂ Antibody Titer | Titer | Blend C Log₂ Antibody Titer | Titer |
|---|---|---|---|---|---|
| Group #1 | | | | | |
| BLP16 Dilipo | 1 | 17.7 | 1/218,700 | 11.4 | 1/2700 |
| 400 μg/mL BP1-217 | 2 | 17.7 | 1/218,700 | <6.6 | <1/100 |
| 200 μg/mL lipid A | 3 | 16.2 | 1/72,900 | 9.8 | 1/900 |
| | 4 | 16.2 | 1/72,900 | 9.8 | 1/900 |
| | 5 | 16.2 | 1/72,900 | 11.4 | 1/2700 |
| Group #2 | | | | | |
| BLP16 Monolipo | 1 | 11.4 | 1/2700 | <6.6 | <1/100 |
| 400 μg/mL BP1-228 | 2 | 9.8 | 1/900 | <6.6 | <1/100 |
| 200 μg/mL lipid A | 3 | 9.8 | 1/900 | <6.6 | <1/100 |
| | 4 | 9.8 | 1/900 | <6.6 | <1/100 |
| | 5 | <6.6 | <1/100 | <6.6 | <1/100 |
| Group #3 | | | | | |
| BLP25 | 1 | 6.6 | 1/100 | <6.6 | <1/100 |
| 400 μg/mL BP1-148 | 2 | <6.6 | <1/100 | <6.6 | <1/100 |
| 200 μg/mL lipid A | 3 | | 1/100 | <6.6 | <1/100 |
| | 4 | <6.6 | <1/100 | 8.2 | 1/300 |
| | 5 | <6.6 | <1/100 | <6.6 | <1/100 |
| Group #4 | | | | | |
| Saline | 1 | <6.6 | <1/100 | <6.6 | <1/100 |
| | 2 | <6.6 | <1/100 | <6.6 | <1/100 |
| | 3 | <6.6 | <1/100 | <6.6 | <1/100 |
| | 4 | 6.6 | 1/100 | <6.6 | <1/100 |
| | 5 | <6.6 | <1/100 | <6.6 | <1/100 |

C57Bl/6 mice were immunized two times with liposomal formulation: BLP16 Dilipo containing MUC1 based lipopeptide (BP1-217) and lipid A, or BLP16 Monolipo containing MUC1 based lipopeptide (BP1-228) and lipid A, or BLP25 containing MUC1 based lipopeptide (BP1-148) and lipid A BP1-217 GVTSAPDTRPAPGSTAS(Myristyl)S(Myristyl)L (SEQ ID NO: 5)

BP1-228 GVTSAPDTRPAPGSTAS(Myristyl)L (SEQ ID NO: 6)

BP1-148 STAPPAHGVTSAPDTRPAPGSTAPP-Lys(Palmitoyl) (SEQ ID NO: 8)

Two immunizations of dilipo-MUC I peptide liposomes stimulates mostly the T2, humoral, immune response, although there remains some cellular immune system activity, as seen by T cell proliferation and IFN-γ production. Nonetheless, the invention shows that liposomal administration of a MUC I peptide with two lipid chains (e.g., either palmitoyl lysine or myristyl serine lipid chains) attached provides a dramatic increase in antibody production and stimulation of the humoral immune system.

This accomplishment has not previously been observed in any mammalian model.

TABLE 2

Protocol 1350B (2x immunization) IgM and IgG Antibody Titer Data

| Injected Material | Mouse # | BP1-151-HSA IgM Titer | BP1-151-HSA IgG Titer | Blend C IgM Titer | Blend C IgG Titer |
|---|---|---|---|---|---|
| BLP24 Dilipo | 1 | 1/72,900 | 1/218,700 | 1/100 | 1/300 |
| 400 µg/mL BP1-132 | 2 | 1/24,300 | 1/218,700 | 1/100 | 1/300 |
| 200 µg/mL lipid A | 3 | 1/8100 | 1/218,700 | 1/100 | 1/900 |
| x2 immunization | 4 | 1/24,300 | 1/218,700 | 1/100 | 1/300 |
| BLP25 | 1 | <6.6 | <1/100 | 1/100 | <1/100 |
| 400 µg/mL BP1-148 | 2 | 6.6 | 1/100 | <1/100 | <1/100 |
| 200 µg/mL lipid A | 3 | 8.2 | 1/300 | 1/100 | <1/100 |
| x2 immunization | 4 | <6.6 | <1/100 | 1/100 | <1/100 |
| Saline | 1 | <6.6 | <1/100 | <1/100 | <1/100 |
| x2 immunization | 2 | <6.6 | <1/100 | <1/100 | <1/100 |
|  | 3 | <6.6 | <1/100 | <1/100 | <1/100 |
|  | 4 | <6.6 | <1/100 | <1/100 | <1/100 |

C57Bl/6 mice were immunized two times with liposomal formulation:
BLP24 Dilipo, containing MUCI based lipopeptide (BP1-132B) and lipid A
BLP25 containing MUC1 based lipopeptide (BP1-148) and lipid A
BP1-132B (SEQ ID NO: 9)
TAPPAHGVTSAPDTRPAPGSTAPPK(Palmitoyl)K(Palmitoyl)L To further characterize the observed phenomenon, MUC I transgenic mice were immunized with MUC I based liposomal formulations containing mono- or dilipopeptides. As shown in Table 3, a strong IgG antibody response was again observed upon immunization with the dilipopeptide (BP1-217), but only after four immunizations. This shows that C57Bl/6 MUC I transgenic mice which are tolerogenic for MUC I antigen need more immunizations than normal C57Bl/6 mice to break this tolerance and induce high levels of anti-MUC I IgG. Mice immunized with only the monolipopeptide (e.g., BP1-228), however, showed very low titers of IgG.

Thus, administration of a liposomal formulation comprising monolipo-MUC I peptide stimulates a cellular response. Immunization with a dilipo-MUC I peptide liposomal formulation induces a humoral response. The creation of a liposome comprising monolipo-MUC I and dilipo-MUC I invokes both cellular and humoral immune responses upon immunization. Hence, modulation of the immune response can be achieved by selectively administering a particular liposomal formulation in a certain order.

TABLE 3

Protocol 1347C - MUC1 Transgenic Mice IgG Antibody Titer Data (4 Immunizations)

| Injected Material | Mouse # | BP1-151 HSA Log$_2$ Titer | BP1-151 HSA Antibody Titer | Blend C Log$_2$ Titer | Blend C Antibody Titer |
|---|---|---|---|---|---|
| Group # 1 | | | | | |
| BLP16 Dilipo | 1 | 16.2 | 1/72,900 | <6.6 | <1/100 |
| 400 µg/mL BP1-217 | 2 | 16.2 | 1/72,900 | 6.6 | 1/100 |
| 200 µg/mL lipid A | 3 | 14.6 | 1/24,300 | <6.6 | <1/100 |
|  | 4 | 16.2 | 1/72,300 | <6.6 | <1/100 |
| Group # 2 | | | | | |
| BLP16 Monolipo | 1 | 8.2 | 1/300 | 8.2 | 1/300 |
| 400 µg/mL BP1-228 | 2 | 9.8 | 1/900 | <6.6 | <1/100 |
| 200 µg/mL lipid A | 3 | 9.8 | 1/900 | 8.2 | 1/300 |
|  | 4 | <6.6 | <1/100 | <6.6 | <1/100 |
| Group # 3 | | | | | |
| BLP25 | 1 | 11.4 | 1/2700 | <6.6 | <1/100 |
| 400 µg/mL BP1-228 | 2 | <6.6 | <1/100 | <6.6 | <1/100 |
| 200 µg/mL lipid A | 3 | 9.8 | 1/900 | <6.6 | <1/100 |
|  | 4 | <6.6 | <1/100 | <6.6 | <1/100 |
| Group # 4 | | | | | |
| Saline | 1 | <6.6 | <1/100 | <6.6 | <1/100 |
|  | 2 | <6.6 | <1/100 | <6.6 | <1/100 |

TABLE 3-continued

Protocol 1347C - MUC1 Transgenic Mice IgG Antibody Titer Data (4 Immunizations)

| Injected Material | Mouse # | BP1-151 HSA | | Blend C | |
|---|---|---|---|---|---|
| | | Log₂ Titer | Antibody Titer | Log₂ Titer | Antibody Titer |
| | 3 | <6.6 | <1/100 | <6.6 | <1/100 |
| | 4 | <6.6 | <1/100 | <6.6 | <1/100 |
| | 5 | <6.6 | <1/100 | <6.6 | <1/100 |

C57Bl/6 MUC1 transgenic mice were immunized four times with liposomal formulation: BLP16 Dilipo containing MUC1 based lipopeptide (BP1-217) and lipid A, or BLP16 Monolipo containing MUC1 based lipopeptide (BP1-228) and lipid A, or BLP25 containing MUC1 based lipopeptide (BP1-148) and lipid A
BP1-217 (SEQ ID NO: 5) GVTSAPDTRPAPGSTAS(Myristyl)S(Myristyl)L
BP1-228 (SEQ ID NO: 6) GVTSAPDTRPAPGSTAS(Myristyl)L
BP1-148 (SEQ ID NO: 8) STAPPAHGVTSAPDTRPAPGSTAPP-Lys(Palmitoyl)

Example 3

Mono- and Dilipidated Tuberculosis Peptides

As was observed for MUC I monolipo- and dilipopeptides, immunization with dilipo-tuberculosis peptide dramatically increased antibody production. See Table 4.

TABLE 4

Immune responses in C57Bl/6 mice immunized two times with tuberculosis lipopeptide based liposomal vaccines

| Vaccine | T cell proliferation (CPM) | SI | IFN-g (pg/mL) | IgG TB dilipopep* | IgM TB dilippopep* |
|---|---|---|---|---|---|
| TB Dilipo | 35064 | 13.2 | 9769 | 1/218,700 | 1/900 |
| TB Monolipo | 19501 | 16.2 | 2276 | 1/24,000 | <1/100 |
| Saline | 633 | 0.6 | 495 | <1/100 | <1/100 |

*TB dilipopeptide DQVHFQPLPPAVVKLSDALIK (SEQ ID NO: 2 was used as a solid phase in ELISA assay.

Two immunizations with dilipo-tuberculosis peptide increased the level of IgG titers dramatically as compared to titers that were induced after immunizations with monolipo-tuberculosis peptide. The results indicate that the presence of two lipids increases the titer that correlates to a humoral response by almost 10 times.

Example 4

Mono- and Dilipidated Hepatitis B Peptides

TABLE 5

Protocol I368B Immune responses in mice immunized two times with hepatitis B mono- or dilipopeptide liposomal vaccine

| Vaccine | T cell proliferation (CPM) | IFN-g (pg/mL) | IgG Hepatitis B dilipopep* | IgM Hepatitis B dilipopep* |
|---|---|---|---|---|
| Hepatitis B Dilipo | 3243 | 0 | 1/48,600 | 1/2700 |
| Hepatitis B Monolipo | 5242 | 1034 | 1/100 | <1/300 |
| Saline | 158 | 361 | <1/100 | <1/100 |

*Hepatitis B dilipopeptide IRTPPAYRPPNAPILK(Palmitate)K(Palmitate)G (SEQ ID NO: 10) was used as a solid phase in ELISA assay.

Two immunizations with dilipo-hepatitis B peptide increased dramatically the level of IgG titers, as compared to the titers that were induced after immunizations with monolipo-hepatitis B peptide. Similarly, the level of IgM antibodies is higher after dilipopeptide liposome formulation is used for immunization procedure.

Example 5

Mono- and Dilipidated Malaria Peptides

TABLE 6

Protocol I368B Immune responses in mice immunized two times with malaria mono- or dilipopeptide liposomal vaccine

| Vaccine | T cell proliferation (CPM) | IFN-g (pg/mL) | IgG Malaria dilipopep* | IgM Malaria dilipopep* |
|---|---|---|---|---|
| Malaria Dilipo | 15075 | 1989 | 1/2700 | 1/2700 |
| Malaria Monolipo | 1280 | 1036 | 1/100 | <1/100 |
| Saline | 74 | 361 | <1/100 | <1/100 |

*Malaria dilipopeptide VTHESYQELVKKLEALEDAVK(Palmitate)K(Palmitate)G (SEQ ID NO: 11) was used as a solid phase in ELISA assay.

Two immunizations with dilipo-malaria peptide increased the level of both IgG and IgM titers, as compared to the titers that were induced after immunizations with monolipo-malaria peptide. In this case malaria dilipopeptide vaccine induced stronger cell proliferation and IFN-γ levels as compared to monolipo-vaccine. This shows that the intensity of an immune response, i.e., the cellular immune response, can be modulated by varying the number of lipids attached to the antigen.

Example 6

Varying the Ratio of Mono- and Dilipopeptides in a Liposome

By incorporating various ratios of mono- and dilipopeptides into liposomes, it is possible to modulate the level and intensity of humoral responses. Table 7 summarizes IgM titers in C57Bl/6 mice after two immunizations with various liposomal constructs. As expected, mice immunized with BLP25 monolipopeptide or saline (group 5 and 6) did not produce any detectable IgM titers. However, all liposomal formulations generated a comparable cellular immune response (data not shown).

The mixture of monolipo- and dilipopeptides at 3:1 ratio, respectively, did not significantly improve antibody titers (group 1); however, there is an increase in antibody titer, as compared to group 1 when mono- and dilipopeptides were incorporated into liposomes at 1:1 ratio. The most intense antibody response was observed in the mice immunized with a liposomal formulation containing MUC1 monolipo- and dilipopeptides at the ratio 1:3 (group 3).

Thus, by incorporating mono- and dilipopeptides at various ratios into liposomes it is possible to modulate the level of humoral responses.

TABLE 7

Protocol 1399B (2x immunization) IgM Antibody Titer Data

| Injected Material x2 immunizations i.d. | C57Bl/6 Mouse # | Log$_2$ Titer | IgM BP1-151-HSA Antibody Titer |
|---|---|---|---|
| Gr. 1 | | | |
| BLP25 Monolipo 300 µg/mL Dilipo 100 µg/mL, 2001 µg/mL Lipid A | 1<br>2<br>3<br>4<br>5 | 6.6<br><6.6<br>6.6<br>8.2<br><6.6 | 1/100<br><1/100<br>1/100<br>1/300<br><1/100 |
| Gr. 2 | | | |
| BLP25 Monolipo 200 µg/mL Dilipo 200 µg/mL, 200- µg/mL Lipid A | 1<br>2<br>3<br>4<br>5 | 6.6<br>6.6<br>8.2<br>6.6<br>8.2 | 1/100<br>1/100<br>1/300<br>1/100<br>1/300 |
| Gr. 3 | | | |
| BLP25 Monolipo 100 µg/mL Dilipo 300 µg/mL, 200 µg/mL Lipid A | 1<br>2<br>3<br>4<br>5 | 9.8<br>14.6<br>11.4<br>9.8<br>13 | 1/900<br>1/24,300<br>1/2700<br>1/900<br>1/8100 |
| Gr. 4 | | | |
| BLP25 Dilipo 400 µg/mL 200 µg/mL Lipid A | 1<br>2<br>3<br>4<br>5 | 9.8<br>9.8<br>11.4<br>11.4<br>9.8 | 1/900<br>1/900<br>1/2700<br>1/2700<br>1/900 |
| Gr. 5 | | | |
| BLP25 Monolipo 400 µg/mL | 1<br>2 | <6.6<br><6.6 | <1/100<br><1/100 |

TABLE 7-continued

Protocol 1399B (2× immunization) IgM Antibody Titer Data

| Injected Material ×2 immunizations i.d. | C57Bl/6 Mouse # | IgM BP1-151-HSA Log₂ Titer | Antibody Titer |
|---|---|---|---|
| 200 μg/mL Lipid A | 3 | <6.6 | <1/100 |
|  | 4 | 6.6 | 1/100 |
|  | 5 | <6.6 | <1/100 |
| Gr. 6 |  |  |  |
| Saline | 1 | <6.6 | <1/100 |
|  | 2 | <6.6 | <1/100 |
|  | 3 | <6.6 | <1/100 |
|  | 4 | <6.6 | <1/100 |
|  | 5 | <6.6 | <1/100 |

Monolipo [BP1-148 (SEQ ID NO: 12): STAPPAHGVTSAPDTRPAPGSTAPP-Lys(Pal)G]
Dilipo [BP1-236 (SEQ ID NO: 13): STAPPAHGVTSAPDTRPAPGSTAPPK(Lipo)K(Lipo)G]

Example 7

The Effect of Lipid Chain Position in MUC1 Lipopeptide on the Humoral Immune Response The demonstration of a potent antibody response after immunization of mice with MUC1 lipopeptide with two liposerine residues attached to the carboxy terminus raises a question if this strong antibody response might be maintained, if the position or number of liposerine residues will be changed.

To answer this question several MUC1 lipopeptide constructs with different liposerine residue placements were synthesized. The data presented in Table 8 shows that only formulation #5, with three liposerine residues at carboxy terminus, was able to generate a potent anti-MUC1 IgG response. The insertion of a three-serine spacer between the two lipid chains (formulation #4) led to the decrease of the level of antibody responses.

Similarly, formulation #2 where only one lipid chain was inserted in the middle of the MUC1 peptide showed some low antibody titers, but those titers were much higher when two liposerine residues were inserted into the central position of MUC1 molecule (formulation #1). Some low antibody titers were observed when the liposerine residues were placed in extreme positions: one on the carboxy terminus and one on the amino terminus (formulation #2).

The strongest antibody responses could be generated when two or three liposerine residues are placed at carboxy terminus. Changing the position of the liposerine residues still maintain some antibody titers, higher than BLP25 or saline (group 6 and 7) but significantly lower as compared to carboxy terminus location.

TABLE 8

Protocol 1405 IgG Antibody titer data

| Injected Material # immunizations | Mouse # | BP1-265 Log₂ Titer | Antibody Titer |
|---|---|---|---|
| Gr. 1 |  |  |  |
| Formulation #1 | 1 | 11.40 | 1/2700 |
| (400 μg/mL BP1- | 2 | 11.40 | 1/2700 |
| 271; 200 ug/mL lipid | 3 | 9.80 | 1/900 |
| A) ×2 | 4 | 13.00 | 1/8100 |
| immunizations - i.d. | 5 | 14.60 | 1/24,300 |
| Gr. 2 |  |  |  |
| Formulation #2 | 1 | <6.6 | <1/100 |
| (400 μg,/mL BP1- | 2 | <6.6 | <1/100 |
| 273; 200 ug/mL lipid | 3 | 8.20 | 1/300 |
| A) ×2 | 4 | 8.20 | 1/300 |
| immunizations - i.d. | 5 | 9.80 | 1/900 |
| Gr. 3 |  |  |  |
| Formulation #3 | 1 | 9.80 | 1/900 |
| (400 μg/mL BP1- | 2 | <6.6 | <1/100 |
| 272; 200 ug/mL lipid | 3 | 8.20 | 1/300 |
| A) ×2 | 4 | 8.20 | 1/300 |
| immunizations - i.d. | 5 | <6.6 | <1/100 |
| Gr. 4 |  |  |  |
| Formulation #4 | 1 | 9.80 | 1/900 |
| (400 μg/mL BP1- | 2 | 8.20 | 1/300 |
| 274; 200 ug/mL lipid | 3 | 13.00 | 1/8100 |
| A) ×2 | 4 | 6.60 | 1/100 |
| immunizations - i.d. | 5 | 11.40 | 1/2700 |
| Gr. 5 |  |  |  |
| Formulation #5 | 1 | 14.60 | 1/24,300 |
| (400 μg/mL BP1- | 2 | 16.20 | 1/72,900 |
| 275; 200 ug/mL lipid | 3 | 16.20 | 1/72,900 |
| A) ×2 | 4 | 16.20 | 1/72,900 |
| immunizations - i.d. | 5 | 16.20 | 1/72,900 |
| Gr. 6 |  |  |  |
| Formulation #6 | 1 | <6.6 | <1/100 |
| (400 μg/mL BP1- | 2 | <6.6 | <1/100 |
| 148; 200 ug/mL lipid | 3 | <6.6 | <1/100 |
| A) ×2 | 4 | 11.40 | 1/2700 |
| immunizations - i.d. | 5 | <6.6 | <1/100 |
| Gr. 7 |  |  |  |
| Saline ×2 | 1 | <6.6 | <1/100 |
| immunizations - i.d. | 2 | <6.6 | <1/100 |
|  | 3 | <6.6 | <1/100 |
|  | 4 | <6.6 | <1/100 |
|  | 5 | <6.6 | <1/100 |

[BP1-265 (SEQ ID NO: 14): TSAPDTRPAPGSTAPPAHGVTSAPDTR-PAPGSTAPPAHGVS(Lipo)S(Lipo)L]
[BP1-271 (SEQ ID NO: 15): TSAPDTRPAPGSS(Lipo)S(Lipo)STSAP-DTRPAPGS]
[BP1-272 (SEQ ID NO: 16): TSAPDTRPAPGSS(Lipo)STSAPDTRPAPGS]
[BP1-273 (SEQ ID NO: 17): S(Lipo)GVTSAPDTRPAPGSAS(Lipo)L]
[BP1-274 (SEQ ID NO: 18): GVTSAPDTRPAPGSTAS(Lipo)SSSS(Lipo)L]
[BP1-275 (SEQ ID NO: 19): GVTSAPDTRPAPGSTAS(Lipo)S(Lipo)S(Lipo)L]
[BP1-148 (SEQ ID NO: 20): STAPDAHGVTSAPDTRPAPGSTAPP-Lys(Palmitoyl)]

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. A liposomal composition comprising a MUC1 dilipopeptide, said dilipopeptide comprising TSAPDTRPAPGS (amino acids 24-35 of SEQ ID NO:1), wherein two amino acids of said dilipopeptide are lipidated and wherein the dilipopeptide is (a) a dilipopeptide selected from the group consisting of BP1-265 (SEQ ID NO:14), BP1-271 (SEQ ID NO:15), BP1-273 (SEQ ID NO:17), BP1-274 (SEQ ID NO:18), and BP1-236 (SEQ ID NO:13), or (b) a dilipopeptide differing from (a) solely by the replacement of at least one lipid group with another lipid group.

2. The composition of claim 1 wherein the dilipopeptide differs from (a) solely by the replacement of at least one lipid group with another lipid group and in which each lipidated amino acid is lipidated with a lipid selected independently from the group consisting of myristyl, palmitoyl and lauryl.

3. The composition of claim 1, which further comprises an adjuvant.

4. The composition of claim 3, wherein the adjuvant is selected from the group consisting of lipid A or a derivative thereof, monophosphoryl lipid A, muramyl dipeptide, and IL-2.

5. The composition of claim 3, wherein the adjuvant is lipid A or a derivative thereof or monophosphoryl lipid A.

6. The composition of claim 1, wherein the dilipopeptide comprises one or more glycosylated amino acids.

7. The composition of claim 1, wherein the dilipopeptide further comprises a MUC 1 carbohydrate linked to serine or threonine of said dilipopeptide.

8. The composition of claim 1, wherein the dilipopeptide is BP1-265 (SEQ ID NO:14).

9. The composition of claim 1, wherein the dilipopeptide is BP1-271 (SEQ ID NO:15).

10. The composition of claim 1, wherein the dilipopeptide is BP1-273 (SEQ ID NO:17).

11. The composition of claim 1, wherein the dilipopeptide is BP1-274 (SEQ ID NO:18).

12. The composition of claim 1, wherein the dilipopeptide is BP1-236 (SEQ ID NO:13).

13. A liposomal composition comprising a MUC1 dilipopeptide, said dilipopeptide comprising TSAPDTRPAPGS (amino acids 24-35 of SEQ ID NO:1), wherein two amino acids of said dilipopeptide are lipidated and said dilipopeptide comprises BP1-265 (SEQ ID NO:14).

\* \* \* \* \*

SEQUENCE LISTING

<160> NUMBER OF SEQ ID NOS: 20

<210> SEQ ID NO 1
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Gly Val Thr Ser Ala Pro Asp Thr Arg Pro Ala Pro Gly Ser Thr
 1               5                  10                  15

Ala Pro Pro Ala His Gly Val Thr Ser Ala Pro Asp Thr Arg Pro Ala
            20                  25                  30

Pro Gly Ser Thr Ala Pro Pro Ala His Gly Val Ser Ser Leu
        35                  40                  45

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Gln Val His Phe Gln Pro Leu Pro Pro Ala Val Val Lys Leu Ser
 1               5                  10                  15

Asp Ala Leu Ile Lys
            20

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Arg Thr Pro Pro Ala Tyr Arg Pro Pro Asn Ala Pro Ile Leu Lys
 1               5                  10                  15

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Thr His Glu Ser Tyr Gln Glu Leu Val Lys Lys Leu Glu Ala Leu
 1               5                  10                  15

Glu Asp Ala Val Lys
            20

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 5

Gly Val Thr Ser Ala Pro Asp Thr Arg Pro Ala Pro Gly Ser Thr Ala
 1               5                  10                  15

Ser Ser Leu

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Val Thr Ser Ala Pro Asp Thr Arg Pro Ala Pro Gly Ser Thr Ala
 1               5                  10                  15

Ser Leu

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Ala Pro Pro Ala His Gly Val Thr Ser Ala Pro Asp Thr Arg Pro
 1               5                  10                  15

Ala Pro Gly Ser Thr Ala Pro Pro Lys Lys Gly
             20                  25

<210> SEQ ID NO 8
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Thr Ala Pro Pro Ala His Gly Val Thr Ser Ala Pro Asp Thr Arg
 1               5                  10                  15

Pro Ala Pro Gly Ser Thr Ala Pro Pro Lys
             20                  25

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Ala Pro Pro Ala His Gly Val Thr Ser Ala Pro Asp Thr Arg Pro
 1               5                  10                  15

Ala Pro Gly Ser Thr Ala Pro Pro Lys Lys Leu
             20                  25

<210> SEQ ID NO 10
<211> LENGTH: 18
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 10

Ile Arg Thr Pro Pro Ala Tyr Arg Pro Pro Asn Ala Pro Ile Leu Lys
 1               5                  10                  15

Lys Gly

<210> SEQ ID NO 11
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Thr His Glu Ser Tyr Gln Glu Leu Val Lys Lys Leu Glu Ala Leu
 1               5                  10                  15

Glu Asp Ala Val Lys Lys Gly
            20

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Thr Ala Pro Pro Ala His Gly Val Thr Ser Ala Pro Asp Thr Arg
 1               5                  10                  15

Pro Ala Pro Gly Ser Thr Ala Pro Pro Lys Gly
            20                  25

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Thr Ala Pro Pro Ala His Gly Val Thr Ser Ala Pro Asp Thr Arg
 1               5                  10                  15

Pro Ala Pro Gly Ser Thr Ala Pro Pro Lys Lys Gly
            20                  25

<210> SEQ ID NO 14
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Ser Ala Pro Asp Thr Arg Pro Ala Pro Gly Ser Thr Ala Pro Pro
 1               5                  10                  15

Ala His Gly Val Thr Ser Ala Pro Asp Thr Arg Pro Ala Pro Gly Ser
            20                  25                  30

Thr Ala Pro Pro Ala His Gly Val Ser Ser Leu

<210> SEQ ID NO 15
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Thr Ser Ala Pro Asp Thr Arg Pro Ala Pro Gly Ser Ser Ser Thr
 1               5                  10                  15
Ser Ala Pro Asp Thr Arg Pro Ala Pro Gly Ser
            20                  25

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Thr Ser Ala Pro Asp Thr Arg Pro Ala Pro Gly Ser Ser Ser Thr Ser
 1               5                  10                  15
Ala Pro Asp Thr Arg Pro Ala Pro Gly Ser
            20                  25

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Ser Gly Val Thr Ser Ala Pro Asp Thr Arg Pro Ala Pro Gly Ser Ala
 1               5                  10                  15
Ser Leu

<210> SEQ ID NO 18
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Gly Val Thr Ser Ala Pro Asp Thr Arg Pro Ala Pro Gly Ser Thr Ala
 1               5                  10                  15
Ser Ser Ser Ser Ser Leu
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

```
Gly Val Thr Ser Ala Pro Asp Thr Arg Pro Ala Pro Gly Ser Thr Ala
 1               5                   10                  15

Ser Ser Ser Leu
            20

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Thr Ala Pro Asp Ala His Gly Val Thr Ser Ala Pro Asp Thr Arg
 1               5                   10                  15

Pro Ala Pro Gly Ser Thr Ala Pro Pro Lys
                20                  25
```